United States Patent

Handa

(10) Patent No.: US 9,068,919 B2
(45) Date of Patent: Jun. 30, 2015

(54) X-RAY IMAGING APPARATUS

(71) Applicant: CANON KABUSHIKI KAISHA, Tokyo (JP)

(72) Inventor: Soichiro Handa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 213 days.

(21) Appl. No.: 13/763,325

(22) Filed: Feb. 8, 2013

(65) Prior Publication Data

US 2013/0208861 A1  Aug. 15, 2013

(30) Foreign Application Priority Data

Feb. 10, 2012  (JP) .................. 2012-027540

(51) Int. Cl.

| | |
|---|---|
| *G01N 23/04* | (2006.01) |
| *A61B 6/00* | (2006.01) |
| *G21K 1/02* | (2006.01) |
| *A61B 6/06* | (2006.01) |

(52) U.S. Cl.
CPC ...... *G01N 23/04* (2013.01); *G21K 1/02* (2013.01); *A61B 6/06* (2013.01); *A61B 6/4035* (2013.01); *A61B 6/4266* (2013.01); *A61B 6/4291* (2013.01); *A61B 6/4452* (2013.01); *A61B 6/484* (2013.01); *G21K 2207/005* (2013.01)

(58) Field of Classification Search
CPC ...... G01N 23/04; A61B 6/4035; A61B 6/484; G21K 2207/005
USPC ...................................... 378/36, 62
See application file for complete search history.

(56) References Cited

U.S. PATENT DOCUMENTS

| | | | |
|---|---|---|---|
| 5,812,629 | A | 9/1998 | Clauser |
| 2002/0044272 | A1 | 4/2002 | Basiji et al. |
| 2004/0085527 | A1 | 5/2004 | Basiji et al. |

FOREIGN PATENT DOCUMENTS

| | | |
|---|---|---|
| JP | 5277093 A | 10/1993 |
| JP | 11276464 A | 10/1999 |
| WO | 9505725 A1 | 2/1995 |

OTHER PUBLICATIONS

Wen et al., "Theory of oblique and grazing incidence Talbot-Lau interferometers and demonstration in a compact source x-ray reflective interferometer", Optics Express, Dec. 5, 2011, 11 pages.

*Primary Examiner* — Courtney Thomas (74) *Attorney, Agent, or Firm* — Canon USA Inc. IP Division (57) ABSTRACT

An X-ray imaging apparatus for imaging an object to be inspected includes a grating that forms a periodic pattern using an X-ray from an X-ray source and a detector that detects the periodic pattern. In the X-ray imaging apparatus, when $\theta 1$ is an angle formed between a first direction, which is a periodic direction of the periodic pattern in a plane that is perpendicular to an optical axis of the X-ray, and a line parallel to an X-ray receiving surface of the detector in the plane, and $\theta 2$ is a grazing angle of the X-ray relative to the X-ray receiving surface, $$\frac{1}{\sqrt{\sin^2\theta_1 \sin^2\theta_2 + \cos^2\theta_1}} > 2$$

holds. Also in the X-ray imaging apparatus, an angle formed between a surface of the grating and the optical axis of the X-ray is from 45 to 90°.

20 Claims, 4 Drawing Sheets

X-RAY IMAGING APPARATUS

BACKGROUND OF THE INVENTION

1. Field of the Invention

The present invention relates to an imaging apparatus utilizing the phase of an X-ray.

2. Description of the Related Art

X-rays, which are highly transmissive through a substance, are widely utilized in medical and industrial fields in image pickup units that capture an image of the inner structure of an object to be inspected. Nowadays, an imaging method, in which the phase shift of an X-ray occurring due to transmission of the X-ray through the object is utilized (X-ray phase imaging), has been studied and developed.

As one of the technologies in which the phase shift of the X-ray is utilized, an imaging technology in which a periodic pattern is formed by utilizing a grating has been proposed. As examples of such a technology, the following methods are known: a method in which the shadow of the grating is projected onto the detector described in International Publication No. WO/1995/005725, and a Talbot interference method described in U.S. Pat. No. 5,812,629.

In the example described in International Publication No. WO/1995/005725, an X-ray is spatially split into a number of beams using a grating, an object to be inspected is irradiated with the split beams, and a periodic pattern formed by the X-ray beams having been transmitted through the object are detected by a detector. The X-ray beams are refracted in accordance with a phase change due to transmission through the object. The refraction causes the positions of the X-ray beams to shift. This positional shift of the X-ray beams can be detected with the detector as a change in the periodic pattern caused by the object.

In the above-described method, the spatial period of the X-ray beams split by the grating is an important parameter that determines the performance and the size of an X-ray imaging apparatus. In general, a comparatively small period of X-ray beams, for example, several tens of µm, is desirable with respect to detection sensitivity for refraction of X-ray beams, spatial resolution, capability of separating information about refraction from information about absorption, the size of the apparatus, and the like.

However, since the spatial resolution of a detector used for X-ray imaging apparatuses is typically several tens of µm or equal to or larger than 100 µm, the period of the X-ray beams needs to be designed in accordance with the spatial resolution of the detector.

In the example described in U.S. Pat. No. 5,812,629, a grating uses a diffraction grating and the phase shift of an X-ray caused by an object to be detected is detected by forming an interference pattern called a self image by utilizing the Talbot effect and detecting a change in the interference pattern formed due to transmission of X-ray beams through the object. In the Talbot interference method, an interference pattern having a several µm period is typically formed on an X-ray receiving surface of a detector separated from the grating by several hundred mm. The interference pattern is one of periodic patterns formed due to interference of the X-ray (light). Such an imaging method is referred to as the Talbot interference method in the field of X-ray phase imaging.

However, the spatial resolution of a detector used for X-ray imaging apparatuses is typically several tens of µm or equal to or larger than 100 µm. Thus, it is difficult to directly detect an interference pattern formed by utilizing a general Talbot interference method.

In order to address the above-described problem, in the technology described in U.S. Pat. No. 5,812,629, a shield grating is provided at a position where the interference pattern is formed. This shield grating has a periodic structure, the period of which is substantially equal to that of the interference pattern. This allows a local change in the interference pattern to be indirectly detected.

However, use of the shield grating causes the apparatus to have a complex structure.

For these reasons, in an X-ray imaging apparatus for imaging the object by using the periodic pattern, it is desired that a periodic pattern with a smaller period can be directly detected by the detector.

SUMMARY OF THE INVENTION

The present invention provides an X-ray imaging apparatus for imaging an object to be inspected by using a periodic pattern of an X-ray and allows a periodic pattern having a smaller period than that detectable by the related art to be directly detected.

An X-ray imaging apparatus for imaging an object to be inspected, according to the present invention includes a grating that forms a periodic pattern using an X-ray from an X-ray source and a detector that detects the periodic pattern. In the X-ray imaging apparatus, when θ1 is an angle formed between a first direction, which is a periodic direction of the periodic pattern in a plane that is perpendicular to an optical axis of the X-ray, and a line parallel to an X-ray receiving surface of the detector in the plane, θ2 is a grazing angle of the X-ray relative to the X-ray receiving surface, $$\frac{1}{\sqrt{\sin^2\theta_1 \sin^2\theta_2 + \cos^2\theta_1}} > 2$$

holds. In the X-ray imaging apparatus, an angle formed between a surface of the grating and the optical axis of the X-ray is from 45 to 90°.

Further features of the present invention will become apparent from the following description of exemplary embodiments with reference to the attached drawings.

DESCRIPTION OF THE EMBODIMENTS

An embodiment according to the present invention will be described in detail below with referent to the drawings. In the drawings, similar elements are denoted by similar reference numerals and redundant description thereof is omitted.

Embodiment

Figure 1:
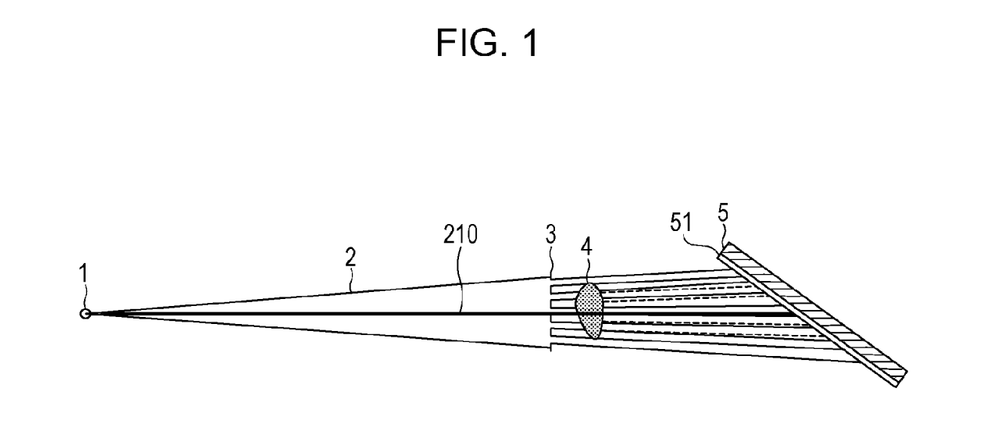
FIG. 1 illustrates an X-ray imaging apparatus according to an embodiment of the present invention.

An X-ray imaging apparatus that projects the shadow of a grating toward a detector will be described as an embodiment of an X-ray imaging apparatus. FIG. 1 illustrates the X-ray imaging apparatus according to the present embodiment. The X-ray imaging apparatus according to the present embodiment includes an X-ray source 1, a grating 3, and a detector 5. The grating 3 splits an X-ray 2 so as to form beams. The detector 5 detects a periodic pattern formed by the grating 3. Results of detection performed by the detector 5 are subjected to a phase recovery process using a computing unit (not shown), so that information about the phase shift of the X-ray due to an object to be inspected can be obtained.

The X-ray source 1 may be an X-ray source that emits a divergent X-ray or an X-ray source that emits a collimated X-ray (for example, synchrotron). Furthermore, the X-ray source 1 may be an X-ray source that emits a characteristic X-ray, or an X-ray source that emits a continuous X-ray. The X-ray source 1 needs to emit such an X-ray 2 that allows a periodic pattern formed by the grating 3 to be contrasted on an X-ray receiving surface 51 of the detector 5.

In the present embodiment, the grating 3 is a splitting element. The splitting element has a transmitting portions that allow the X-ray to be transmitted therethrough and shielding portions that block the X-ray. The transmitting portions and the blocking portions are periodically arranged so as to spatially split the X-ray 2, thereby forming X-ray beams. The splitting element thus forms X-ray beams, thereby forming on the X-ray receiving surface 51 of the detector 5 a periodic pattern in a first-direction-corresponding direction.

Herein, a periodic pattern refers to not only a pattern having a uniform period but also a pattern, the period of which regularly changes. For example, a pattern having bright portions, the pitch of which outwardly increases from a central portion, is still referred to as a periodic pattern. In order to calculate information about the object from a result of detection performed by the detector 5, the period of a periodic pattern formed on the X-ray receiving surface 51 can be uniform. However, when a change in a pattern caused by the object can be detected, information about the object can also be obtained using a pattern having a non-uniform period. A first direction refers to a periodic direction of a periodic pattern 24 on a plane perpendicular to an optical axis 210. The first-direction-corresponding direction refers to a direction on the X-ray receiving surface 51, the direction being formed when the first direction is projected onto the X-ray receiving surface 51. When seen from the X-ray source 1, a first direction 22 and a first-direction-corresponding direction 220 superpose on each other. The optical axis 210 of the X-ray 2 refers to a line that connects the center of the X-ray source 1 (X-ray emitting portion of the X-ray source 1) and the center of an area irradiated with the X-ray 2 on the X-ray receiving surface 51 of the detector 5 to each other. Although it is not illustrated in FIG. 1, in the case where the X-ray imaging apparatus includes an aperture for the X-ray 2 between the X-ray source 1 and the object, a line that passes through the X-ray source 1 and the center of the aperture matches the optical axis 210 of the X-ray 2.

An angle formed between the surface of the grating 3 and the optical axis 210 of the X-ray 2 is preferably from 45 to 90°, and more preferably, from 60 to 90°.

As an angle formed between the surface of the grating 3 and the optical axis 210 decreases, an incident angle of the X-ray 2 with respect to the grating 3 at an intersection of the grating 3 and the optical axis 210 increases and a grazing angle decreases. This decreases the area of the grating 3 seen from the X-ray source 1, thereby decreasing an effective area of the grating 3.

Furthermore, gratings are generally designed and fabricated on an assumption that the gratings are arranged perpendicular to the optical axis. Thus, as an angle formed between a grating and the optical axis decreases, a periodic pattern intended in the design becomes unlikely to be obtained. For example, depending on the aspect ratio of the structure of the grating and the incident angle of the X-ray, the entirety of the X-ray incident upon the grating may be transmitted through part of an X-ray absorber included in the blocking portions while passing through the grating. This may lead to a situation in which a contrast of the periodic pattern is decreased or the entirety of the X-ray is uniformly blocked, and accordingly, the periodic pattern is not formed.

The phases of the X-ray are changed while being transmitted through an object to be inspected 4, thereby changing a traveling direction of the X-ray. This causes the detection position of each of the split X-ray beams to shift. An angle at which the X-ray is refracted can be calculated in accordance with the amount of the above-described shift in position. Since a refraction angle can be regarded as an inclination angle of a wavefront of light, a distribution of inclination amounts of the wavefront can be obtained through such a calculation. The shape of the wavefront can also be obtained by numerically integrating the obtained wavefront inclination distribution. Since the wavefront shape can also be regarded as a distribution of phase shift amounts of the X-ray due to transmission of the X-ray through the object, the wavefront shape may also be referred to as a phase image. Likewise, since the wavefront inclination distribution is a distribution of spatial differential values of the wavefront shape, the wavefront inclination distribution may also be referred to as a differential phase image. Thus, such a phase image and a differential phase image can be an image of the object 4 obtained by utilizing phase information of the X-ray that has been transmitted through the object 4.

Although the object 4 is positioned between the grating 3 and the detector 5 in FIG. 1, the object 4 may be positioned between the X-ray source 1 and the grating 3.

In the present embodiment, the detector 5 is an indirect-conversion flat panel detector and includes the X-ray receiving surface 51, an X-ray conversion layer (scintillator layer) 52, and an image pickup device 53. Although it is different from the present embodiment, a direct-conversion flat panel detector may be used instead of the indirect-conversion flat panel detector. In the case of the direct-conversion detector, the detector includes an X-ray receiving surface and an X-ray conversion layer (photoelectric conversion layer) and detects the X-ray having been converted into an electrical signal by the X-ray conversion layer.

In the X-ray imaging apparatus according to the present embodiment, the detector 5 is arranged such that the X-ray beams are obliquely incident upon the X-ray receiving surface 51 of the detector 5. Thus, the periodic pattern formed on the X-ray receiving surface 51 is magnified. This allows the detector 5 to directly detect a periodic pattern, the period of which is smaller than that in the case where the X-ray beams are perpendicularly incident upon the X-ray receiving surface 51.

Magnification of the periodic pattern attributable to oblique incidence is described below with reference to FIGS. 2A to 2C. Here, the grating 3 is assumed to include a one-dimensional grating having slits arranged in a row and spaced apart from one another by a constant period. It is also assumed that the angle formed between the surface of the grating 3 and the optical axis 210 is 90°. In such a case, the split X-ray beams are sheet-shaped multiple beams.

Figure 2A:
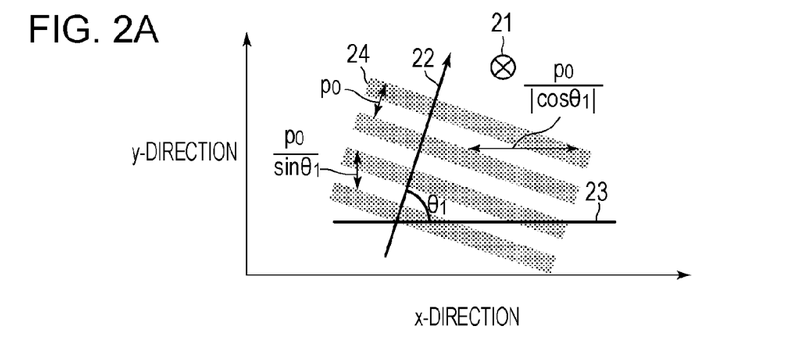
FIG. 2A illustrates a periodic pattern in a plane perpendicular to the optical axis of an X-ray according to the embodiment of the present invention.

FIG. 2A illustrates the periodic pattern 24 in a plane perpendicular to the optical axis 210 of the X-ray.

Figure 2B:
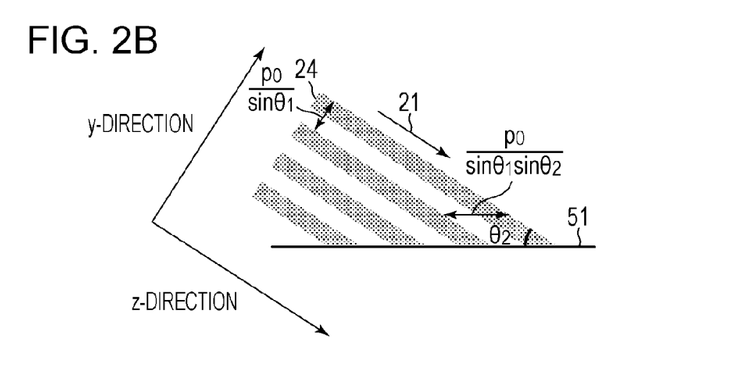
FIG. 2B illustrates a periodic pattern in a plane parallel to the optical axis of the X-ray and perpendicular to an X-ray receiving surface according to the embodiment of the present invention.
Figure 2C:
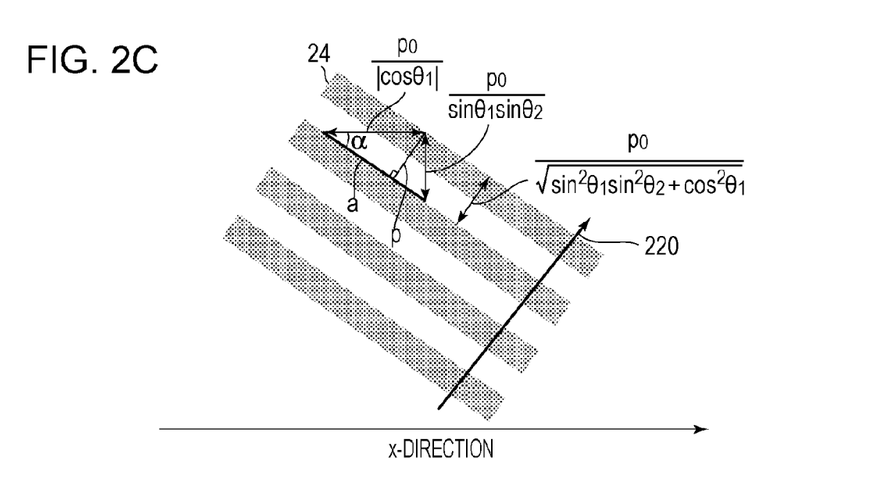
FIG. 2C illustrates a periodic pattern on the X-ray receiving surface according to the embodiment of the present invention.

Since FIGS. 2A to 2C are enlarged views near the optical axis 210, the X-ray incidence direction 21 is assumed to be parallel to the optical axis 210. Accordingly, in FIG. 2A, the X-ray incidence direction 21 is perpendicular to the page of the drawing. In the plane perpendicular to the optical axis 210, a period p0 is a period in the periodic direction 22 (first direction) of the periodic pattern 24 at a position where the X-ray receiving surface 51 is arranged. Next, the period at the position where the X-ray receiving surface 51 is arranged is described.

In the case where the X-ray 2 incident upon the grating 3 is a collimated X-ray, p0 is not affected by the distance between the X-ray source 1 and the grating 3 or the distance between the grating 3 and the X-ray receiving surface 51. In contrast, in the case where the X-ray 2 incident upon the grating 3 is a divergent X-ray, the periodic pattern is magnified in accordance with the distance between the X-ray source 1 and the grating 3 and the distance between the grating 3 and the X-ray receiving surface 51. For example, in FIG. 1, since the magnification factor in an upper portion and a lower portion of the X-ray receiving surface 51 are different from each other due to divergence of the X-ray 2, to be exact, p0 in the upper portion and p0 in the lower portion are different from each other. The period in the periodic direction 22 of the periodic pattern 24 at the position where the X-ray receiving surface 51 is arranged is, in other words, a pitch of the periodic pattern 24 in the periodic direction 22 in a plane that is perpendicular to the optical axis 210 of the X-ray and intersects the X-ray receiving surface 51. p0 can be obtained by multiplying a period of a periodic pattern formed when the grating 3 is irradiated with the collimated X-ray 2 by the magnification factor attributable to divergence of the X-ray 2. Since p0 is, as described above, the period of the periodic pattern 24 in the plane perpendicular to the optical axis 210, p0 can also be understood as a period of a pattern on an X-ray receiving surface, the pattern being formed when the X-ray is perpendicularly incident upon the X-ray receiving surface.

An angle formed between the periodic direction 22 and a line 23 in the plane perpendicular to the optical axis 210 of the X-ray is defined as angle θ1. The line 23 represents one of lines parallel to the X-ray receiving surface 51. In FIG. 2A, the periods of the periodic pattern 24 in the lengthwise direction (y-axis direction) and the widthwise direction (x-axis direction) can be respectively expressed as p0/sin θ1 and p0/|cos θ1| (where 0°<θ1<180°.

FIG. 2B illustrates the X-ray receiving surface 51 and the periodic pattern 24 (X-ray beams) on a plane parallel to the optical axis 210 and perpendicular to the X-ray receiving surface 51. Since FIG. 2B is an enlarged view, the X-ray beams that form the periodic pattern 24 are substantially parallel to each other. Thus, the X-ray beams are approximated that they are parallel to each other in the drawing. Also in FIG. 2B, θ2 is an angle formed between the X-ray receiving surface 51 and the X-ray incidence direction on the plane and a grazing angle of the X-ray. The X-ray incidence direction refers to a direction in which a certain area of the X-ray receiving surface 51 and the X-ray source 1 are connected to each other with a straight line.

It can be seen from FIG. 2B that the period of the periodic pattern 24 in the widthwise direction of the drawing (direction parallel to the X-ray receiving surface 51 in a plane parallel to the X-ray incidence direction 21 and perpendicular to the X-ray receiving surface 51) can be expressed as follows: p0/(sin θ1 sin θ2).

FIG. 2C illustrates the periodic pattern 24 on the X-ray receiving surface 51. The widthwise direction of FIG. 2C corresponds to the widthwise direction (x-axis direction) of FIG. 2A, and the lengthwise direction in FIG. 2C corresponds to the widthwise direction of FIG. 2B. Similar to FIG. 2B, FIG. 2C is also an enlarged view of the center of the area irradiated with the X-ray and the area around the center on the X-ray receiving surface 51. Since variation in the magnification factor attributable to divergence of the X-ray is assumed to be negligible, the pitch of the periodic pattern 24 is illustrated as a uniform pitch. From FIG. 2C, the following expression holds:

$$a = \sqrt{\frac{p_0^2}{|\cos\theta_1|^2} + \frac{p_0^2}{\sin^2\theta_1 \sin^2\theta_2}}$$

$$= \sqrt{\frac{p_0^2(\sin^2\theta_1 \sin^2\theta_2 + \cos^2\theta_1)}{\cos^2\theta_1 \sin^2\theta_1 \sin^2\theta_2}}$$

$$= \frac{p_0\sqrt{\sin^2\theta_1 \sin^2\theta_2 + \cos^2\theta_1}}{|\cos\theta_1||\sin\theta_1\sin\theta_2|}.$$

Thus, the period p in the first-direction-corresponding direction 220 of the periodic pattern 24 on the X-ray receiving surface 51 is expressed as follows:

$$p = \frac{p_0}{|\cos\theta_1|}\sin\alpha$$

$$= \frac{p_0}{|\cos\theta_1|}\left(\frac{p_0}{\sin\theta_1 \sin\theta_2}\frac{1}{a}\right)$$

$$= \frac{p_0}{|\cos\theta_1|}\frac{p_0}{\sin\theta_1\sin\theta_2}\frac{|\cos\theta_1||\sin\theta_1\sin\theta_2|}{p_0\sqrt{\sin^2\theta_1\sin^2\theta_2 + \cos^2\theta_1}}$$

$$= \frac{p_0}{\sqrt{\sin^2\theta_1 \sin^2\theta_2 + \cos^2\theta_1}}.$$

Accordingly, the pattern period p, which is a period on the X-ray receiving surface 51 in the case where the X-ray is incident in an arbitrary direction other than the perpendicular direction, is magnified at a magnification factor of M with respect to the pattern period P0, which is a pattern period in the case where the X-ray is incident in a perpendicular direction, and expressed as p=Mp0. Thus, from the above-described expression, the following expression holds:

$$M = \frac{1}{\sqrt{\sin^2\theta_1 \sin^2\theta_2 + \cos^2\theta_1}}.$$

Hereafter, this magnification factor may be referred to as a magnification factor attributable to oblique incidence.

The magnification factor attributable to oblique incidence of the X-ray has been described with an example of the enlarged view of the center of the area irradiated with the X-ray and the area around the center on the X-ray receiving surface 51. The description is approximately applicable also to other areas on the X-ray receiving surface 51 except for θ2, and p0, in which the magnification factor attributable to divergence of the X-ray is reflected. θ2 and p0 differ among areas on the X-ray receiving surface 51. For example, when the grating 3 and the detector 5 are disposed as illustrated in FIG. 1, θ2 becomes closer to 90° and p0 decreases from lower to upper portions in FIG. 1.

In order to detect the periodic pattern 24 by the detector 5, the length of the period of the periodic pattern 24 on the X-ray receiving surface 51 in the first-direction-corresponding direction 220 needs to be equal to or larger than the minimum length resolvable by the detector 5 in the first-direction-corresponding direction 220 (referred to as spatial resolution hereafter). When written in an expression, the following expression holds:

$$\frac{p_0}{\sqrt{\sin^2\theta_1 \sin^2\theta_2 + \cos^2\theta_1}} \geq R. \qquad \text{expression (1)}$$

where R represents the spatial resolution of the detector 5 in the first-direction-corresponding direction 220. The above-described expression (1) can hold for the whole area of the X-ray receiving surface 51. In the X-ray imaging apparatus as illustrated in FIG. 1, the upper an area is in the X-ray receiving surface 51, that is, the closer θ2 of the area is to 90°, the smaller the left side of the expression (1) is, that is, the smaller the period of the periodic pattern 24 on the X-ray receiving surface 51 in the first-direction-corresponding direction 220 is. Thus, on the X-ray receiving surface 51, when the expression (1) holds in an area where θ2 is close to 90°, it can be regarded that the expression (1) holds in the whole area of the X-ray receiving surface 51. The whole area of the X-ray receiving surface 51 refers to a whole area of the X-ray receiving surface 51, the area being used for imaging. In order to detect the X-ray, in general, an intensity distribution of the periodic pattern can be more precisely detected when the length of the period of the periodic pattern is twice or larger than the spatial resolution.

In order to directly detect a periodic pattern having a smaller period than that of a related-art periodic pattern, the following expression can hold:

$$M = \frac{1}{\sqrt{\sin^2\theta_1 \sin^2\theta_2 + \cos^2\theta_1}} > 2.$$

The above-described expression can hold with respect to the whole area of the X-ray receiving surface 51. In order for the magnification factor attributable to oblique incidence to become greater than 2, it is sufficient, for example, when θ1 is 90°, θ2 be larger than 0° and smaller than 30°. As is the case with the expression (1), when M is greater than 2 in an area where θ2 is close to 90°, it can be regarded that M is greater than 2 in the whole area of the X-ray receiving surface 51. When θ1 is a constant value, M increases as θ2 becomes closer to 0°, and accordingly, a periodic pattern having a smaller period can be detected. Thus, θ2 is preferably smaller than 15°, and more preferably smaller than 10°. However, as θ2 becomes closer to 0°, the area of the X-ray receiving surface 51 seen from the X-ray source 1 decreases, and accordingly, the size of the field of view decreases. Thus, θ2 is preferably larger than 2°.

Figure 3:
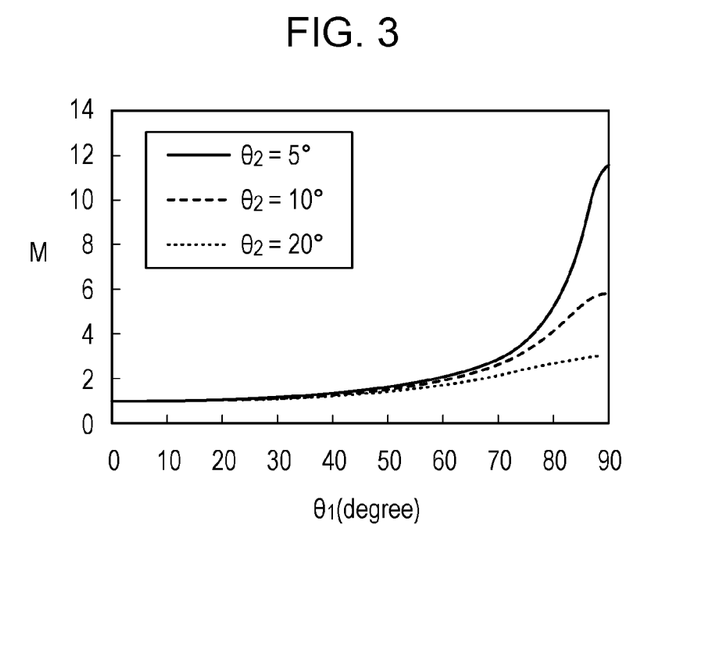
FIG. 3 is a graph illustrating the relationships between magnification factors attributable to oblique incidence and angles with respect to the incidence direction according to the embodiment of the present invention.

FIG. 3 is a graph illustrating the relationships between θ1 and the magnification factor M attributable to oblique incidence when θ2 is 5°, 10°, and 20°. As illustrated in FIG. 3, M monotonically increases with respect to θ1 in a range of 0°<θ1<90°, and reaches the maximum value, 1/sin θ2, when θ1 is 90°. A curve representing M in a range of 90°<θ1<180° is equal to a lateral inversion of a curve in the range 0°<θ1<90°. Thus, when other conditions are fixed, the period of the periodic pattern 24 on the X-ray receiving surface 51 becomes the maximum when θ1=90°. Accordingly, when the spatial resolution of the detector 5 is assumed to be isotropic on the X-ray receiving surface 51 and does not change depending on the incidence direction of the X-ray, contrast detected becomes the maximum when θ1=90°. Thus, θ1 is preferably close to 90°. Also as can be seen from FIG. 3, as θ2 decreases, the range of θ1 with which M becomes close to the maximum value, 1/sin θ2, decreases. More specifically, in order for M to become substantially close to the maximum value, 1/sin θ2, |90°−θ1|<θ2 needs to be satisfied. Thus, θ1 and θ2 can satisfy this expression.

Figure 4:
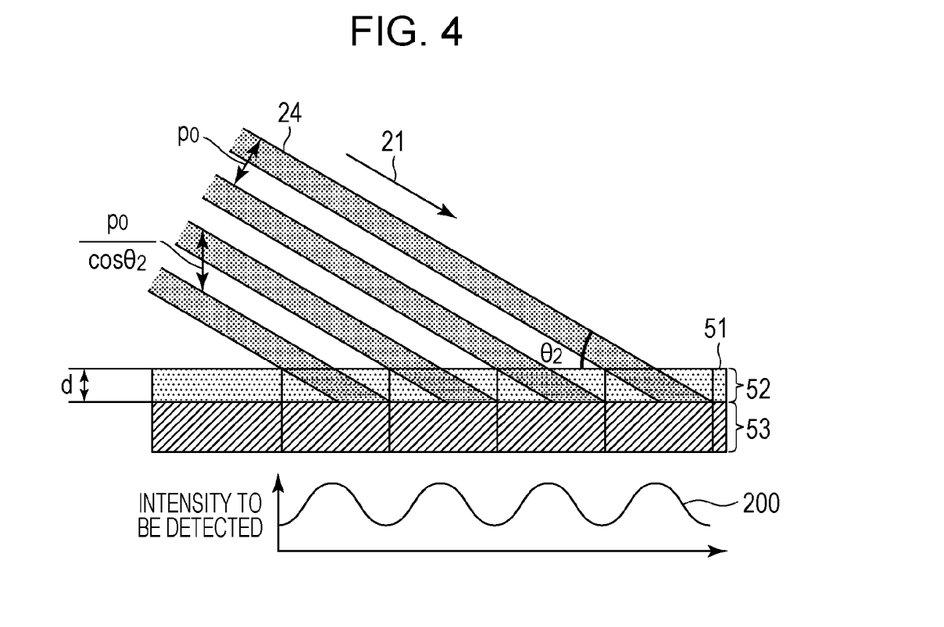
FIG. 4 illustrates the relationship between a grazing angle of split beams and the thickness of an X-ray conversion layer of a detector according to the embodiment of the present invention.

FIG. 4 illustrates the sections of the periodic pattern 24 and the detector 5 on the same plane as that illustrated in FIG. 2B. In FIG. 4, a case in which θ1=90°, where M reaches the maximum, with θ2 regarded as a constant is assumed. As described above, the detector 5 according to the present embodiment includes the X-ray receiving surface 51, the X-ray conversion layer 52, and the image pickup device 53. In FIG. 4, the thickness d of the X-ray conversion layer 52 is p0/(2 cos θ2). This thickness is equal to ½ of p0/cos θ2, which is the period of the periodic pattern 24 in the lengthwise direction on the plane illustrated in FIG. 4. Under the above-described conditions, the intensity of the X-ray detect by the image pickup device 53 is generally thought to be so distributed as an intensity distribution 200. Thus, when the pixel size of the image pickup device 53 is assumed to be sufficiently small with respect to the period of the intensity distribution 200, the detector 5 can detect individual beams in a spatially separated manner. As described above, in the periodic pattern 24, when the bright portions (portions where the X-ray intensity is high) and the dark portions (portions where the X-ray intensity is low) have the same width, the thickness d of the X-ray conversion layer 52 of the detector 5 is preferably equal to or smaller than p0/(2 cos θ2). Also when, in the periodic pattern 24, the bright portions and the dark portions have different widths, the thickness d of the X-ray conversion layer 52 of the detector 5 can be smaller than the width of the dark portions in the lengthwise direction of the plane illustrated in FIG. 4. In other words, when the ratio of width of the dark portions to the period p0/cos θ2 of the periodic pattern 24 in the lengthwise direction of the plane illustrated in FIG. 4 is c/e, the thickness of the X-ray conversion layer 52 of the detector 5 is preferably smaller than the length of the p0/cos θ2 multiplied by c/e. When the bright portions and the dark portions have the same width, c/e is ½.

In the X-ray imaging apparatus according to the present embodiment, by performing the phase recovery process using a result of detection performed by the detector 5, information (differential phase image and phase image) about the object 4 can be obtained. The phase recovery process is performed by the computing unit. It is sufficient that the computing unit can perform computation. The computation unit may use, for example, a computer. The phase recovery process may use, for example, the Fourier transform method. The details of the Fourier transform method are described in the following article and description thereof is omitted herein: Mitsuo Takeda, et al., J. Opt. Soc. Am. Vol. 72, No. 1 (1982). Alternatively, the phase recovery process may use the phase shift method with a plurality of images captured while moving the position of the grating 3 in the in-plane direction. The details of the phase shift method are described in the following document and description thereof is omitted herein: Chapter 14, Optical Shop Testing, Second Edition, and ed. by Daniel Malacara, John Wiley and Sons, 1992. A scattering image and an absorption image of the object 4 can also be obtained depending on a calculation performed by the computer.

In the present embodiment, the X-ray imaging apparatus as illustrated in FIG. 1, with which the following method of capturing images is performed, has been described. That is, the grating 3 splits the X-ray to form the beams, a shadow of the grating 3 is directly projected onto the X-ray receiving surface 51, so that the periodic pattern 24 is formed on the X-ray receiving surface 51. Instead of directly projecting the shadow of the grating 3, the periodic pattern 24 may be formed on the X-ray receiving surface 51 by utilizing the Talbot effect. This method is the aforementioned Talbot interference method.

When using the Talbot interference method, the periodic pattern 24 is formed by a diffraction grating using the Talbot effect and the X-ray receiving surface 51 of the detector 5 is disposed near the position where the periodic pattern 24 is formed. The object 4 is positioned between the X-ray source 1 and the grating or the grating and the detector 5. The periodic pattern 24 formed by the Talbot effect is a periodic pattern generated by the X-ray beams interfering with each other, the X-ray beams being diffracted by the diffraction grating, with each other. Thus, the periodic pattern 24 that includes information about refraction of the X-ray 2 by the object 4 is detected. The diffraction grating may use an X-ray shield grating (amplitude-type diffraction grating) that periodically blocks the X-ray 2 or an X-ray phase grating (phase-type diffraction grating) that periodically shifts the phase of the X-ray 2. In terms of the amount of X-ray radiation, the phase grating has an advantage in that the phase grating allows a larger amount of X-ray radiation to be transmitted therethrough than the shield grating. In general, when the Talbot effect is utilized, a grating or a periodic pattern with a shorter period can be used compared to a method where the shadow of the grating is directly projected onto the detector 5.

Alternatively, the Lau effect may be utilized instead of use of a small-focus X-ray source. In this case, by disposing a source grating between the X-ray source 1 and the grating 3, a state in which a plurality of linear X-ray sources are arranged is virtually formed. The source grating typically has a structure in which narrow slits are equally spaced apart from one another. By appropriately selecting the spatial period of the slits, periodic patterns formed by the X-ray beams that have passed through the individual slits become superposed with one another by being shifted by an integer multiple of the pattern period. As a result, the intensity of the pattern can be improved while maintaining the contrast of the pattern. When using the source grating, the focal spot size of the X-ray source 1 can be increased. This allows the amount of X-ray radiation per unit time to increase. Furthermore, use of the source grating prevents the contrast of the periodic pattern 24 from decreasing due to vibration of the focal spot position.

In the present embodiment, the grating 3 is assumed to have a one-dimensional periodic structure. However, the grating 3 and the above-described source grating may have a two-dimensional periodic structure. For example, the grating may have a mesh-shaped pattern in which two periodic components having periodic directions being different from each other by 90° are formed. When using a grating having such a two-dimensional periodic structure, a two-dimensional periodic pattern having periods in a first direction and a second direction that intersects the first direction can be formed.

When detecting a two-dimensional periodic pattern, out of the periods in the first and second directions included in the periodic pattern, which of the periods is magnified by oblique incidence so as to form the periodic pattern on the X-ray receiving surface 51 can be selected in accordance with arrangement of the X-ray receiving surface 51 of the detector 5.

Alternatively, after the periodic pattern has been detected by causing the X-ray receiving surface 51 to assume a first orientation in order to magnify the period in the first direction using oblique incidence, the periodic pattern may be detected by changing the orientation of the X-ray receiving surface 51 into a second orientation in order to magnify the period in the second direction using oblique incidence. By doing this, the periods in two directions of the periodic pattern can be directly detected. Thus, refraction angles of the X-ray with respect to the first and second directions can be calculated. The change in the orientation of the X-ray receiving surface 51 from the first to second orientation may be performed using an orientation adjustment unit that adjusts the orientation of the X-ray receiving surface 51. The orientation adjustment unit may use, for example, an orientation adjustment instruction unit and an actuator that receives a signal from the orientation adjustment instruction unit to move the orientation of the X-ray receiving surface 51.

When the X-ray receiving surface 51 is disposed obliquely to the grating 3 as illustrated in FIG. 1, the distance between the X-ray receiving surface 51 and the grating 3 varies. In FIG. 1, the distance between the X-ray receiving surface 51 and the grating 3 is smaller in an upper portion of the page of the drawing than a lower portion of the page of the drawing. When the above-described variation in distance occurs, the magnification factor of the periodic pattern 24 varies due to divergence of the X-ray as described above. In order to address this problem, a measure that corrects the difference in pattern period on the basis of positions may be taken when the shift amounts of beam positions are calculated. Alternatively, the period on the grating 3 may be inclined in advance by considering the magnification factor attributable to divergence of the X-ray, thereby decreasing variation in the period of the periodic pattern 24 formed on the X-ray receiving surface 51.

Figure 5A:
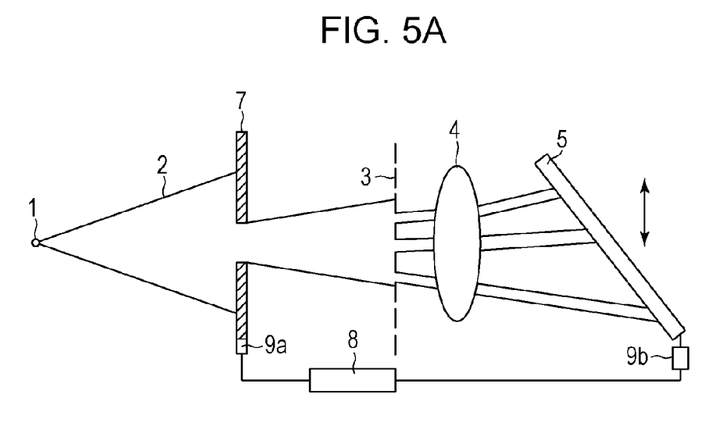
FIG. 5A illustrates a modification of the X-ray imaging apparatus according to the embodiment of the present invention.
Figure 5B:
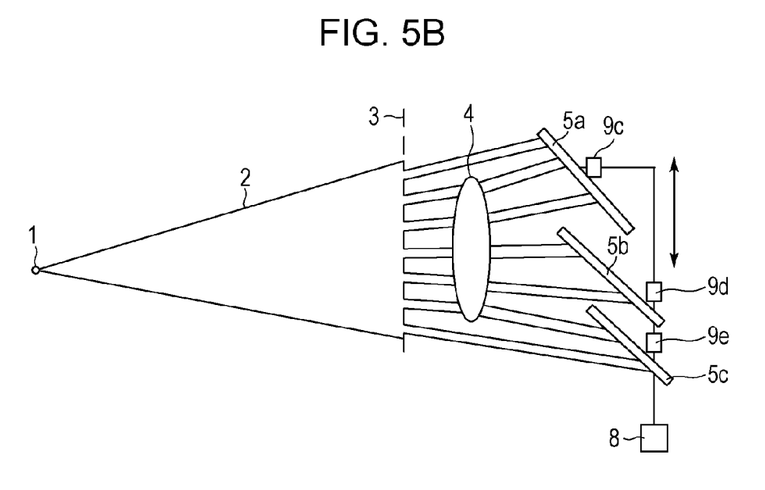
FIG. 5B illustrates a modification of the X-ray imaging apparatus according to the embodiment of the present invention.

When the X-ray receiving surface 51 of the detector is arranged in an oblique incidence position, compared to a case where the X-ray receiving surface 51 is disposed so that the X-ray is perpendicularly incident upon the X-ray receiving surface 51, the detection area of the detector 5 decreases. This causes an image capturing area (effective field of view) of the X-ray imaging apparatus to decrease. In order to address this problem, as illustrated in FIG. 5A, a mechanism that allows the detector 5 to move (scan) so as to detect the X-ray a plurality of times may be provided, or, as illustrated in FIG. 5B, a plurality of the detectors 5 may be provided in the X-ray imaging apparatus. The X-ray imaging apparatus illustrated in FIG. 5A includes a shutter 7 that has an opening, a movement instruction unit 8 as a movement unit that causes the shutter 7 and the detector 5 to move, and actuators 9 (9a and 9b). The shutter 7 and the X-ray receiving surface 51 are moved in directions indicated by a double-headed arrow in FIG. 5A using the movement instruction unit 8 and the actuators 9. The shutter 7 allows part of the X-ray 2 to be incident upon the X-ray receiving surface 51, to be transmitted through the opening and blocks the other part of the X-ray 2. Thus, the amount of X-ray radiation to which the object 4 is exposed can be decreased compared to the case where the shutter 7 is not provided.

When the plurality of detectors 5 (5a, 5b, and 5c) are disposed like the X-ray imaging apparatus illustrated in FIG. 5B, the number of times detection is performed can be decreased compared to the case where a single detector 5 is moved to repeatedly perform detection as illustrated in FIG. 5A. In the X-ray imaging apparatus illustrated in FIG. 5B, the X-ray receiving surface 51 can be scanned as similarly to the X-ray imaging apparatus illustrated in FIG. 5A. For this purpose, the X-ray imaging apparatus illustrated in FIG. 5B includes the movement instruction unit 8 and the actuators 9 (9c, 9d, and 9e). Instead of using the plurality of detector 5 that each have a single X-ray receiving surface 51, a detector including a plurality of X-ray receiving surfaces 51 may be used. In the X-ray imaging apparatuses as illustrated in FIGS. 5A and 5B, the image capturing area can be increased compared to the X-ray imaging apparatus illustrated in FIG. 1. In order to ensure an image capturing area of the same size, the X-ray imaging apparatus illustrated in FIG. 5A or 5B can use a detector having a smaller X-ray receiving surface. This also allows variation in the magnification factor and θ2 due to divergence of the X-ray 2 to be decreased.

The grating 3 may be moved so as to perform detection a plurality of times like the detector 5 in FIG. 5A. However, the structure of the X-ray imaging apparatus, which causes only the detector 5 to move, can be simple compared to the X-ray imaging apparatus in which the detector 5 and the grating 3 are moved in a synchronized manner. Furthermore, when seen from the X-ray source 1, the area of the grating 3 may appear smaller than that of the detection area depending on the angle formed between the grating 3 and the optical axis 210. In this case, the area, an image of which can be captured in a single shot, is restricted by the area of the grating 3 seen from the X-ray source 1, and accordingly, the times the image is captured increases. For this reason, the angle formed between the surface of the grating 3 and the optical axis 210 is preferably from 45 to 90°. A plurality of the gratings 3 may be provided like the detectors 5 in FIG. 5B. Also in this case, in order to prevent the number of the gratings from increasing, the angle formed between the surface of the grating 3 and the optical axis 210 of the X-ray 2 is preferably from 45 to 90°.

As described above, in the X-ray imaging apparatus according to the present embodiment, a periodic pattern having a smaller period than that detectable by the related art can be directly detected by disposing the detector 5 such that the X-ray beams are obliquely incident upon the X-ray receiving surface 51 of the detector 5.

Thus, when an imaging method in which the shadow of the grating is directly projected onto the detector is performed, X-ray beams, the period of which is smaller than that of the related art, can be used.

In the Talbot method, an interference pattern, which is a fine periodic pattern, can be directly detected depending on the magnification factors (the magnification factor attributable to oblique incidence and the magnification factor attributable to divergence of the X-ray) of the periodic pattern. A related-art Talbot method is known, in which a Moire formed by using an interference pattern and the shield grating in combination is detected. However, when forming a Moire using the shield grating, the amount of X-ray radiation that reaches the X-ray receiving surface is generally decreased due to blocking with the grating. Furthermore, in many cases, the contrast of a Moire detected is lower than that of a periodic pattern on which the Moire is based. As in the case of the aforementioned Fourier transform method, the shift amounts of positions may be calculated from local intensity distribution of a periodic pattern in order to calculate the shift amounts of beam positions from the periodic pattern. However, when using such a method, the spatial resolution of the X-ray imaging apparatus with respect to a periodic direction of a Moire is restricted by the period of the Moire.

When an interference pattern is directly detected by using the X-ray imaging apparatus according to the present embodiment, problems as described above can be addressed as well as simplifying the structure of the X-ray imaging apparatus.

EXAMPLES

First Example

An X-ray imaging apparatus as a first example of the present invention will be described below. The X-ray imaging apparatus of the present example is one example according the above-described embodiment.

In the present example, the X-ray source 1 uses a rotating anode-type X-ray source using a tungsten target. The X-ray source generates a cone-beam shaped X-ray at a tube voltage of 35 kV. An aluminum plate of 1 mm thickness is used as a filter for the X-ray in order to block a low energy component. The grating 3 is disposed at a position separated from the X-ray source 1 by 1.1 m at such an angle that the X-ray is perpendicularly incident upon a central portion of the grating 3. The grating 3 is a one-dimensional grating in which slits are arranged in a row at a uniform period. The width and the period of the slits are 10 μm and 20 μm, respectively. The X-ray blocking portions of the grating 3 are formed of gold having a thickness of 100 μm. The X-ray receiving surface 51 of the detector 5 is disposed downstream of the grating 3. The X-ray receiving surface 51 is disposed at such an angle that θ1 and θ2 are respectively 90° and 9.6° relative to an X-ray sheet beam incident upon the center thereof. The X-ray receiving surface 51 is positioned such that the center thereof is at a position 0.5 m downstream of the grating 3. The detector is an indirect-conversion flat panel detector. The thickness of a scintillator layer and the pixel size of the detector 5 are respectively 12 μm and 45 μm. A source grating is disposed 1 m upstream of the grating 3, that is, 0.1 m from the X-ray source 1, at an angle at which the X-ray is perpendicularly incident upon the center of the source grating. The source grating is a one-dimensional grating similar to the grating 3, and an X-ray blocking portion thereof is formed of gold having a thickness of 100 μm. The slit width and the period of the source grating are respectively 15 μm and 60 μm. The object 4 is positioned downstream of the grating 3.

When an image is captured using the above-described X-ray imaging apparatus without the object 4 positioned, a significant pattern change in the periodic pattern due to diffraction does not occur on the X-ray receiving surface 51, and a periodic pattern, the shape of which is the projection of the shadow of the grating 3 onto the X-ray receiving surface 51 without substantially being changed, is formed on the X-ray receiving surface 51. Since the X-ray having passed through the individual slits of the source grating radially spreads, the pattern period (p0 in FIG. 2A) in a plane perpendicular to the incidence direction is enlarged to 30 μm at the center of the X-ray receiving surface 51. Since the magnification factor M attributable to oblique incidence calculated from the values of θ1 and θ2 is 6.0, the period on the periodic pattern detected at and near the center of the X-ray receiving surface 51 is about 180 μm. Thus, this periodic pattern is thought to be detectable using the detector 5 with the above-described pixel size and the above-described thickness of the scintillator layer.

The X-ray 2 is detected with the object 4 positioned in the X-ray imaging apparatus of the present example, and a phase recovery process is performed by analyzing the shift amounts of beam positions using the Fourier transform method in accordance with results from the detection. An image (a differential phase image or a phase image) of the object 4 in accordance with a distribution of the phase shift amount of the X-ray having passed through the object 4 can be obtained. A scattering image and an absorption image of the object 4 can also be obtained according to need.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-027540, filed Feb. 10, 2012, which is hereby incorporated by reference herein in its entirety.

What is claimed is:

1. An X-ray imaging apparatus for imaging an object to be inspected, the apparatus comprising:
   a grating that forms a periodic pattern using an X-ray from an X-ray source; and
   a detector that detects the periodic pattern,
   wherein, when θ1 is an angle formed between a first direction and a line, the first direction being a periodic direction of the periodic pattern in a plane perpendicular to an optical axis of the X-ray, the line being parallel to an X-ray receiving surface of the detector in the plane, and θ2 is a grazing angle of the X-ray relative to the X-ray receiving surface, $$\frac{1}{\sqrt{\sin^2\theta_1 \sin^2\theta_2 + \cos^2\theta_1}} > 2$$

holds, and
   wherein an angle formed between a surface of the grating and the optical axis of the X-ray is from 45 to 90°.

2. The X-ray imaging apparatus according to claim 1, wherein the angle formed between the surface of the grating and the optical axis of the X-ray is from 60 to 90°.

3. The X-ray imaging apparatus according to claim 1, wherein |90°−θ1|<θ2.

4. The X-ray imaging apparatus according to claim 1, wherein the grating is a diffraction grating that causes the X-ray to diffract, and wherein the periodic pattern is an interference pattern formed by beams of the diffracted X-ray interfering with one another.

5. The X-ray imaging apparatus according to claim 1, wherein a plurality of the X-ray receiving surfaces are provided.

6. The X-ray imaging apparatus according to claim 1, wherein the detector includes an X-ray conversion layer, and wherein, when p0 is a pitch of the periodic pattern in the first direction in a plane that is perpendicular to the optical axis of the X-ray and intersects the X-ray receiving surface, a thickness of the X-ray conversion layer is equal to or smaller than p0/(2 cos θ2).

7. The X-ray imaging apparatus according to claim 1, further comprising:
   an orientation adjustment unit that adjusts an orientation of the X-ray receiving surface,
   wherein the periodic pattern also has a period in a second direction that intersects the first direction,
   wherein the orientation adjustment unit causes the X-ray receiving surface to assume a first orientation and a second orientation that is different from the first orientation, and
   wherein the detector detects the periodic pattern when the X-ray receiving surface is in the first orientation and when the X-ray receiving surface is in the second orientation.

8. An X-ray imaging apparatus for imaging an object to be inspected, the apparatus comprising:
   a grating that forms a periodic pattern using an X-ray from an X-ray source; and
   a detector that detects the periodic pattern,
   wherein, when θ1 is an angle formed between a first direction and a line, the first direction being a periodic direction of the periodic pattern in a plane that is perpendicular to an optical axis of the X-ray, the line being parallel to an X-ray receiving surface of the detector in the plane, θ2 is a grazing angle of the X-ray relative to the X-ray receiving surface, p0 is a pitch of the periodic pattern in the first direction in a plane that is perpendicular to the optical axis of the X-ray and intersects the X-ray receiving surface, and R is a minimum resolvable length on the X-ray receiving surface in a direction corresponding to the first direction, θ2 is greater than 0° and smaller than 30°, and $$\frac{p_0}{\sqrt{\sin^2\theta_1 \sin^2\theta_2 + \cos^2\theta_1}} \geq R$$

holds, and
   wherein an angle formed between a surface of the grating and the optical axis of the X-ray is from 45 to 90°.

9. The X-ray imaging apparatus according to claim 8, wherein the angle formed between the surface of the grating and the optical axis of the X-ray is from 60 to 90°.

10. The X-ray imaging apparatus according to claim 8, wherein |90°−θ1|<θ2.

11. The X-ray imaging apparatus according to claim 8, wherein the grating is a diffraction grating that causes the X-ray to diffract, and wherein the periodic pattern is an interference pattern formed by beams of the diffracted X-ray interfering with one another.

12. The X-ray imaging apparatus according to claim 8, wherein a plurality of the X-ray receiving surfaces are provided.

13. The X-ray imaging apparatus according to claim 8, wherein the detector includes an X-ray conversion layer, and
   wherein, a thickness of the X-ray conversion layer is equal to or smaller than p0/(2 cos θ2).

14. The X-ray imaging apparatus according to claim 8, further comprising:

an orientation adjustment unit that adjusts an orientation of the X-ray receiving surface, wherein the periodic pattern also has a period in a second direction that intersects the first direction, wherein the orientation adjustment unit causes the X-ray receiving surface to assume a first orientation and a second orientation that is different from the first orientation, and wherein the detector detects the periodic pattern when the X-ray receiving surface is in the first orientation and when the X-ray receiving surface is in the second orientation.

15. An X-ray apparatus comprising:

a grating that forms a periodic pattern using an X-ray from an X-ray source; and a detector that detects the periodic pattern, wherein, when θ1 is an angle formed between a first direction and a line, the first direction being a periodic direction of the periodic pattern in a plane perpendicular to an optical axis of the X-ray, the line being parallel to an X-ray receiving surface of the detector in the plane, and θ2 is a grazing angle of the X-ray relative to the X-ray receiving surface, $$\frac{1}{\sqrt{\sin^2\theta_1 \sin^2\theta_2 + \cos^2\theta_1}} > 2$$

holds.

16. The X-ray imaging apparatus according to claim 15, wherein |90°−θ1|<θ2.

17. The X-ray imaging apparatus according to claim 15, wherein the detector includes an X-ray conversion layer, and wherein, when p0 is a pitch of the periodic pattern in the first direction in a plane that is perpendicular to the optical axis of the X-ray and intersects the X-ray receiving surface, a thickness of the X-ray conversion layer is equal to or smaller than p0/(2 cos θ2).

18. An X-ray apparatus comprising:

a grating that forms a periodic pattern using an X-ray from an X-ray source; and a detector that detects the periodic pattern, wherein, when θ1 is an angle formed between a first direction and a line, the first direction being a periodic direction of the periodic pattern in a plane that is perpendicular to an optical axis of the X-ray, the line being parallel to an X-ray receiving surface of the detector in the plane, θ2 is a grazing angle of the X-ray relative to the X-ray receiving surface, p0 is a pitch of the periodic pattern in the first direction in a plane that is perpendicular to the optical axis of the X-ray and intersects the X-ray receiving surface, and R is a minimum resolvable length on the X-ray receiving surface in a direction corresponding to the first direction, θ2 is greater than 0° and smaller than 30°, and $$\frac{p_0}{\sqrt{\sin^2\theta_1 \sin^2\theta_2 + \cos^2\theta_1}} \geq R$$

holds.

19. The X-ray imaging apparatus according to claim 18, wherein |90°−θ1|<θ2.

20. The X-ray imaging apparatus according to claim 18, wherein the detector includes an X-ray conversion layer, and wherein, a thickness of the X-ray conversion layer is equal to or smaller than p0/(2 cos θ2).

* * * * *